(12) United States Patent
Buettelmann et al.

(10) Patent No.: US 7,452,909 B2
(45) Date of Patent: *Nov. 18, 2008

(54) IMIDAZOLE DERIVATIVES

(75) Inventors: Bernd Buettelmann, Schopfheim (DE); Simona Maria Ceccarelli, Basel (CH); Georg Jaeschke, Basel (CH); Sabine Kolczewski, Rheinfelden (DE); Richard Hugh Philip Porter, Reinach (CH); Eric Vieira, Frenkendorf (CH)

(73) Assignee: Hoffman-La Roche Inc., Nutley, NJ (US)

( * ) Notice: Subject to any disclaimer, the term of this patent is extended or adjusted under 35 U.S.C. 154(b) by 296 days.

This patent is subject to a terminal disclaimer.

(21) Appl. No.: 10/926,670

(22) Filed: Aug. 26, 2004

(65) Prior Publication Data

US 2005/0054686 A1 Mar. 10, 2005

(30) Foreign Application Priority Data

Sep. 4, 2003 (EP) .................................. 03019604

(51) Int. Cl.
*A61K 31/4439* (2006.01)
*C07D 401/14* (2006.01)

(52) U.S. Cl. .................. 514/333; 546/256; 546/274.7; 546/275.1; 514/341

(58) Field of Classification Search .......... 546/256, 546/274.7, 275.1; 514/333, 341
See application file for complete search history.

(56) References Cited

U.S. PATENT DOCUMENTS

| | | | |
|---|---|---|---|
| 7,091,222 B2 * | 8/2006 | Buettelmann et al. | 514/341 |
| 7,153,874 B2 * | 12/2006 | Buettelmann et al. | 514/341 |
| 7,241,760 B2 | 7/2007 | Buettelmann et al. | |
| 2004/0248888 A1 | 12/2004 | Buettelmann et al. | |
| 2004/0259917 A1 * | 12/2004 | Cosford et al. | 514/341 |

FOREIGN PATENT DOCUMENTS

| | | |
|---|---|---|
| WO | WO 91/00277 A1 | 1/1991 |
| WO | WO 01/16121 A1 | 3/2001 |

OTHER PUBLICATIONS

Mutel, Vincent, Expert Opin. Ther. Patents, 12, pp. 1845-1852 (2002).
Cliff et al., Synthesis, pp. 681-682 (1994).
Schlaeger et al., Cytotechnology, 30, pp. 71-83 (1999).
Porter et al., Br. J. Pharmacol., 128, pp. 13-20 (1999).

* cited by examiner

*Primary Examiner*—Patricia L Morris
(74) *Attorney, Agent, or Firm*—George W. Johnston; Patricia S. Rocha-Tramaloni; Gene J. Yao

(57) ABSTRACT

The present invention relates to imidazole derivatives of formula I

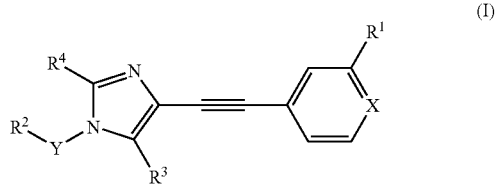

wherein $R^1$, $R^2$, $R^3$, $R^4$, X, Y and R are described hereinabove, or a pharmaceutically acceptable salt thereof. The invention also relates to a pharmaceutical composition comprising the imidazole derivatives of formula I, a process for preparing a compound of formula I, and a method of treating or preventing acute and/or chronic neurological disorder comprising administering to a patient in need of such treatment and/or prevention a therapeutically effective amount of said pharmaceutical composition. These disorders include Alzheimer's disease. These disorders also include mild cognitive impairment.

3 Claims, No Drawings

IMIDAZOLE DERIVATIVES

FIELD OF THE INVENTION

The present invention relates to imidazole derivatives of formula I

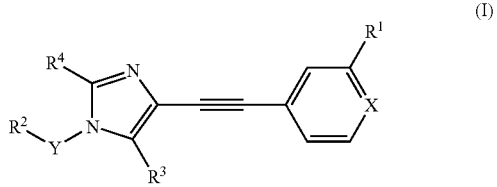

wherein $R^1$, $R^2$, $R^3$, $R^4$, X, Y and R are described hereinbelow, or a pharmaceutically acceptable salt thereof. The invention also relates to a pharmaceutical composition comprising the imidazole derivatives of formula I, a process for preparing a compound of formula I, and a method of treating or preventing acute and/or chronic neurological disorder comprising administering to a patient in need of such treatment and/or prevention a therapeutically effective amount of said pharmaceutical composition. These disorders include Alzheimer's disease. These disorders also include mild cognitive impairment.

BACKGROUND OF THE INVENTION

In the central nervous system (CNS) the transmission of stimuli takes place by the interaction of a neurotransmitter, which is sent out by a neuron, with a neuroreceptor.

Glutamate is the major excitatory neurotransmitter in the brain and plays a unique role in a variety of central nervous system (CNS) functions. The glutamate-dependent stimulus receptors are divided into two main groups. The first main group, namely the ionotropic receptors, forms ligand-controlled ion channels. The metabotropic glutamate receptors (mGluR) belong to the second main group and, furthermore, belong to the family of G-protein coupled receptors.

At present, eight different members of these mGluR are known and of these some even have sub-types. According to their sequence homology, signal transduction mechanisms and agonist selectivity, these eight receptors can be sub-divided into three sub-groups:

mGluR1 and mGluR5 belong to group I, mGluR2 and mGluR3 belong to group II and mGluR4, mGluR6, mGluR7 and mGluR8 belong to group III.

Ligands of metabotropic glutamate receptors belonging to the first group can be used for the treatment or prevention of acute and/or chronic neurological disorders such as psychosis, epilepsy, schizophrenia, Alzheimer's disease, cognitive disorders and memory deficits, as well as chronic and acute pain.

Other treatable indications in this connection are restricted brain function caused by bypass operations or transplants, poor blood supply to the brain, spinal cord injuries, head injuries, hypoxia caused by pregnancy, cardiac arrest and hypoglycemia. Further treatable indications are ischemia, Huntington's chorea, amyotrophic lateral sclerosis (ALS), dementia caused by AIDS, eye injuries, retinopathy, idiopathic parkinsonism or parkinsonism caused by pharmaceutical preparations, i.e., medicaments, as well as conditions which lead to glutamate-deficiency functions, such as e.g. muscle spasms, convulsions, migraine, urinary incontinence, nicotine addiction, opiate addiction, anxiety, vomiting, dyskinesia and depressions.

Disorders mediated full or in part by mGluR5 are for example acute, traumatic and chronic degenerative processes of the nervous system, such as Alzheimer's disease, senile dementia, Parkinson's disease, Huntington's chorea, amyotrophic lateral sclerosis and multiple sclerosis, psychiatric diseases such as schizophrenia and anxiety, depression, pain, drug dependency, smoking cessation und ethanol dependence (*Expert Opin. Ther. Patents* (2002), 12, (12)).

Selective mGluR5 antagonists are especially useful for the treatment of anxiety and pain.

SUMMARY OF THE INVENTION

This invention relates to a compound of formula I

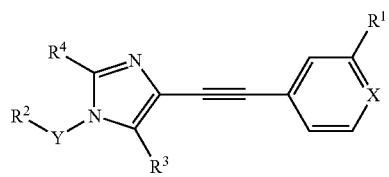

wherein
$R^1$ is selected from halogen, lower alkyl, lower alkoxy, $CF_3$ and cyano;
$R^2$ is selected from
   aryl;
   aryl substituted by one or more substituents selected from the group selected from lower alkyl, halogen, lower alkoxy, $CF_3$ and cyano;
   heteroaryl; and
   heteroaryl substituted by one or more substituents selected from the group consisting of lower alkyl, halogen, lower alkoxy, $CF_3$ and cyano;
$R^3$ is selected from hydrogen, C(O)H and $CH_2R^5$, wherein $R^5$ is selected from hydrogen, OH, $C_1$-$C_6$-alkyl and $C_3$-$C_{12}$-cycloalkyl;
$R^4$ is lower alkyl or $C_3$-$C_{12}$-cycloalkyl;
X is N or CH;
Y is —(CHR)$_{1, 2\ or\ 3}$
R is hydrogen or lower alkyl;
or a pharmaceutically acceptable salt thereof.

The invention also relates to a process for preparing a compound according to formula I.

Moreover, the invention also relates to pharmaceutical compositions containing a compound of formula I and a pharmaceutically acceptable excipient for the treatment and prevention of mGluR5 receptor mediated disorders, such as acute and/or chronic neurological disorders, in particular anxiety and chronic or acute pain.

The invention also relates to a method of treating or preventing acute or chronic neurological disorder comprising administering to a patient in need of such treatment a pharmaceutical composition comprising a therapeutically effective amount of at least one compound of formula I. In particular, the pharmaceutical composition is used for the treatment or prevention of mGluR5 receptor mediated disorders.

DETAILED DESCRIPTION OF THE INVENTION

The following definitions of general terms used in the present description apply irrespective of whether the terms in question appear alone or in combination. The term "lower alkyl" used in the present description denotes straight-chain or branched saturated hydrocarbon residues with 1 to 6 carbon atoms, preferably with 1 to 4 carbon atoms, such as methyl, ethyl, n-propyl, i-propyl, n-butyl, t-butyl and the like.

The term "lower alkoxy" denotes an —O-$C_{1-6}$ alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers.

The term "cycloalkyl" denotes a saturated carbocyclic group, containing 3-12, and preferably 3-6 carbon atoms.

The term "halogen" denotes fluorine, chlorine, bromine and iodine.

The term "aryl" denotes a monovalent cyclic aromatic hydrocarbon radical consisting of one or more fused rings in which at least one is aromatic in nature and which may comprise from 5 to 12 carbon atoms as ring members, for example phenyl, benzyl, naphthyl, biphenyl or indanyl.

The term "heteroaryl" denotes a monovalent aromatic carbocyclic radical, containing at least one heteroatom and which may comprise from 3 to 11 carbon atoms as ring members, and one two or three heteroatom(s), for example pyridyl, pyrazinyl, pyrimidinyl, pyridazinyl or triazinyl.

The term "pharmaceutically acceptable salt" refers to any salt derived from an inorganic or organic acid or base.

The term "therapeutically effective amount" refers to an amount of at least one imidazole derivative compound of formula I, or a pharmaceutically acceptable salt thereof, that modulates the mGluR5 receptors.

The term "pharmaceutically acceptable excipient" refers to a pharmaceutically acceptable carrier, vehicle, diluent, adjustment or similar mechanism for delivering a pharmaceutical composition.

In one embodiment, this invention relates to a compound of formula I

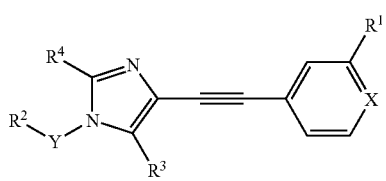

wherein
R¹ is selected from halogen, lower alkyl, lower alkoxy, $CF_3$ and cyano;
R² is selected from
aryl;
aryl substituted by one or more substituents selected from the group selected from lower alkyl, halogen, lower alkoxy, $CF_3$ and cyano;
heteroaryl; and
heteroaryl substituted by one or more substituents selected from the group consisting of lower alkyl, halogen, lower alkoxy, $CF_3$ and cyano;
R³ is selected from hydrogen, C(O)H and $CH_2R^5$, wherein R⁵ is selected from hydrogen, OH, $C_1$-$C_6$-alkyl and $C_3$-$C_{12}$-cycloalkyl;
R⁴ is lower alkyl or $C_3$-$C_{12}$-cycloalkyl;
X is N or CH;
Y is —$(CHR)_{1,2\ or\ 3}$
R is hydrogen or lower alkyl;
or a pharmaceutically acceptable salt thereof.

In another embodiment, this invention relates to a process for preparing a compound of formula I

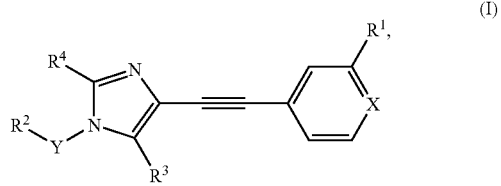

or a pharmaceutically acceptable salt thereof, which process comprises reacting a compound of formula

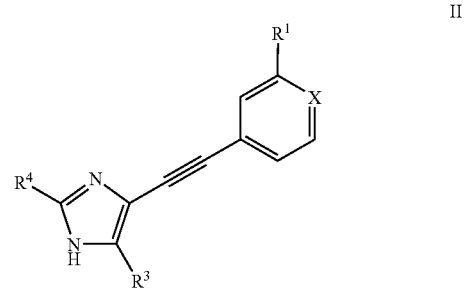

or a pharmaceutically acceptable salt thereof, with a compound of formula $R^2Yhal$ to form the compound of formula I, or a pharmaceutically acceptable salt thereof, wherein
R¹ is selected from halogen, lower alkyl, lower alkoxy, $CF_3$ and cyano;
R² is selected from
aryl;
aryl substituted by one or more substituents selected from the group consisting of lower alkyl, halogen, lower alkoxy, $CF_3$ and cyano;
heteroaryl; and
heteroaryl substituted by one or more substituents selected from the group consisting of lower alkyl, halogen, lower alkoxy, $CF_3$ and cyano;
R³ is selected from hydrogen, C(O)H and $CH_2R^5$, wherein R⁵ is selected from hydrogen, OH, $C_1$-$C_6$-alkyl and $C_3$-$C_{12}$-cycloalkyl;
R⁴ is lower alkyl or $C_3$-$C_{12}$-cycloalkyl;
X is N or CH;
Y is —$(CHR)_{1,2\ or\ 3}$;
R is hydrogen or lower alkyl; and
hal is halogen.

In yet another embodiment, this invention relates to a pharmaceutical composition comprising a compound of formula I

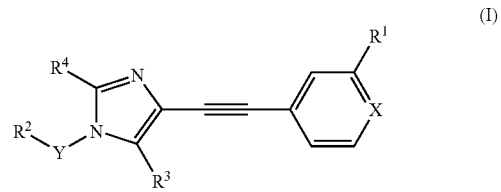

wherein
R$^1$ is selected from halogen, lower alkyl, lower alkoxy, CF$_3$ and cyano;
R$^2$ is selected from
aryl;
aryl substituted by one or more substituents selected from the group consisting of lower alkyl, halogen, lower alkoxy, CF$_3$ and cyano;
heteroaryl; and
heteroaryl substituted by one or more substituents selected from the group consisting of lower alkyl, halogen, lower alkoxy, CF$_3$ and cyano;
R$^3$ is selected from hydrogen, C(O)H and CH$_2$R$^5$, wherein R$^5$ is selected from hydrogen, OH, C$_1$-C$_6$-alkyl and C$_3$-C$_{12}$-cycloalkyl;
R$^4$ is lower alkyl or C$_3$-C$_{12}$-cycloalkyl;
X is N or CH;
Y is —(CHR)$_{1,2\ or\ 3}$
R is hydrogen or lower alkyl;
or a pharmaceutically acceptable salt thereof;
and a pharmaceutically acceptable excipient.

In yet another embodiment, this invention relates to a method of treating or preventing acute or chronic neurological disorder comprising administering to a patient in need of such treatment a pharmaceutical composition comprising a therapeutically effective amount of at least one compound of formula I

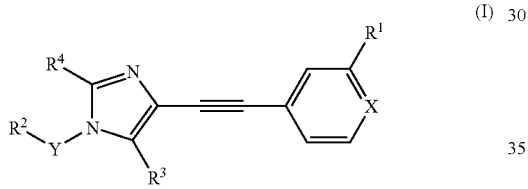

(I)

wherein
R$^1$ is selected from halogen, lower alkyl, lower alkoxy, CF$_3$ and cyano;
R$^2$ is selected from
aryl;
aryl substituted by one or more substituents selected from the group consisting of lower alkyl, halogen, lower alkoxy, CF$_3$ and cyano;
heteroaryl; and
heteroaryl substituted by one or more substituents selected from the group consisting of lower alkyl, halogen, lower alkoxy, CF$_3$ and cyano;
R$^3$ is selected from hydrogen, C(O)H and CH$_2$R$^5$, wherein R$^5$ is selected from hydrogen, OH, C$_1$-C$_6$-alkyl and C$_3$-C$_{12}$-cycloalkyl;
R$^4$ is lower alkyl or C$_3$-C$_{12}$-cycloalkyl;
X is N or CH;
Y is —(CHR)$_{1,2\ or\ 3}$
R is hydrogen or lower alkyl;
or a pharmaceutically acceptable salt thereof.

One embodiment of this invention is directed to a compound of formula I, wherein R$^1$ is lower alkyl, halogen or cyano; R$^2$ is heteroaryl; R$^3$ is hydrogen; R$^4$ is lower alkyl X is N or CH; Y is —(CHR)$_{1,2\ or\ 3}$ and R is hydrogen.

Another embodiment of this invention is directed to a compound of formula I, wherein R$^1$ is lower alkyl, halogen or cyano; R$^2$ is heteroaryl substituted by lower alkyl; R$^3$ is hydrogen; R$^4$ is lower alkyl; X is N or CH; Y is —(CHR)$_{1,2\ or\ 3}$ and R is hydrogen.

Another embodiment of this invention is directed to a compound of formula I, wherein R$^1$ is lower alkyl, halogen or cyano; R$^2$ is heteroaryl substituted by halogen; R$^3$ is hydrogen; R$^4$ is lower alkyl; X is N or CH; Y is —(CHR)$_{1,2\ or\ 3}$ and R is hydrogen.

Another embodiment of this invention is directed to a compound of formula I, wherein R$^1$ is lower alkyl or halogen; R$^2$ is aryl; R$^3$ is hydrogen; R$^4$ is lower alkyl; X is N; Y is —(CHR)$_{1,2\ or\ 3}$ and R is hydrogen.

Another embodiment of this invention is directed to a compound of formula I, wherein R$^1$ is lower alkyl; R$^2$ is aryl substituted by halogen; R$^3$ is hydrogen; R$^4$ is lower alkyl; X is N; Y is —(CHR)$_{1,2\ or\ 3}$ and R is hydrogen.

Preferred compounds of this invention are those compounds wherein R$^4$ is lower alkyl and still preferably methyl.

Among these compounds, especially preferred compounds are those compounds wherein
R$^1$ signifies halogen, lower alkyl, lower alkoxy, CF$_3$ or cyano;
R$^2$ signifies aryl or heteroaryl, optionally substituted by one or more substituents selected from the group consisting of lower alkyl, halogen, lower alkoxy, CF$_3$ or cyano;
R$^3$ signifies H;
R$^4$ signifies methyl;
X signifies N or CH;
Y signifies —(CHR)$_{1,2\ or\ 3}$ and
R signifies hydrogen or lower alkyl;
as well as pharmaceutically acceptable salts thereof.

Especially preferred are those compounds, wherein R$^1$, R$^3$, R$^4$, Y and R are as defined above; X is CH and R$^2$ is pyridyl, optionally substituted by lower alkyl or halogen, for example the following compounds:
2-[4-(3-chloro-phenylethynyl)-2-methyl-imidazol-1-ylmethyl]-pyridine,
2-[4-(3-chloro-phenylethynyl)-2-methyl-imidazol-1-ylmethyl]-6-methyl-pyridine,
5-[4-(3-chloro-phenylethynyl)-2-methyl-imidazol-1-ylmethyl]-2-methyl-pyridine, and
3-[1-(5-chloro-pyridin-3-ylmethyl)-2-methyl-1H-imidazol-4-ylethynyl]-benzonitrile.

Especially preferred are further those compounds, wherein R$^1$, R$^3$, R$^4$, Y and R are as defined above; X is N and R$^2$ is pyridyl, optionally substituted by lower alkyl or halogen, for example the following compounds:
4-[1-(6-methyl-pyridin-2-ylmethyl)-2-methyl-1H-imidazol-4-ylethynyl]-2-methyl-pyridine,
4-[1-(6-methyl-pyridin-2-ylmethyl)-2-methyl-1H-imidazol-4-ylethynyl]-2-chloro-pyridine,
4-[1-(2-methyl-pyridin-5-ylmethyl)-2-methyl-1H-imidazol-4-ylethynyl]-2-chloro-pyridine,
4-[1-(5-chloro-pyridin-3-ylmethyl)-2-methyl-1H-imidazol-4-ylethynyl]-2-methyl-pyridine,
4-[1-(2-Chloro-pyridin-5-ylmethyl)-2-methyl-1H-imidazol-4-ylethynyl]-2-chloro-pyridine, and
4-[1-(2-chloro-pyridin-5-ylmethyl)-2-methyl-1H-imidazol-4-ylethynyl]-2-methyl-pyridine.

Further preferred are those compounds, wherein R$^1$, R$^3$, R$^4$, Y and R are as defined above; X is N and R$^2$ is phenyl, optionally substituted by halogen, for example the following compounds:
4-(1-benzyl-2-methyl-1H-imidazol-4-ylethynyl)-2-methyl-pyridine,
4-(1-benzyl-2-methyl-1H-imidazol-4-ylethynyl)-2-chloro-pyridine, rac-2-methyl-4-[2-methyl-3-(1-phenyl-ethyl)-3H-imida-
  zol-4-ylethynyl]-pyridine,
(+)-2-methyl-4-[2-methyl-3-(1-phenyl-ethyl)-3H-imida-
  zol-4-ylethynyl]-pyridine,
(−)-2-methyl-4-[2-methyl-3-(1-phenyl-ethyl)-3H-imida-
  zol-4-ylethynyl]-pyridine,
rac-2-chloro-4-[2-methyl-1-(1-phenyl-ethyl)-1H-imida-
  zol-4-ylethynyl]-pyridine,
4-[3-(4-fluoro-benzyl)-2-methyl-3H-imidazol-4-ylethy-
  nyl]-2-methyl-pyridine,
4-[3-(3,4-difluoro-benzyl)-2-methyl-3H-imidazol-4-yl-
  ethynyl]-2-methyl-pyridine, and
2-methyl-4-(2-methyl-1-phenethyl-1H-imidazol-4-yl-
  ethynyl)-pyridine.

Further preferred are those compounds, wherein $R^1$, $R^3$, $R^4$, and X are as defined above; Y signifies —(CHR)$_{1,2\ or\ 3}$, with R is lower alkyl. In this case Y forms 1, 2 or 3 chiral center(s). These chiral center(s) allow(s) optical isomers such as enantiomers or racemates of the compounds of the invention. It is understood that these optical isomers or racemates are also encompassed by the instant invention. Among the above recited compounds, examples of such enantiomers or racemates are the following compounds:

rac-2-methyl-4-[2-methyl-3-(1-phenyl-ethyl)-3H-imida-
  zol-4-ylethynyl]-pyridine,
(+)-2-methyl-4-[2-methyl-3-(1-phenyl-ethyl)-3H-imida-
  zol-4-ylethynyl]-pyridine,
(−)-2-methyl-4-[2-methyl-3-(1-phenyl-ethyl)-3H-imida-
  zol-4-ylethynyl]-pyridine, and
rac-2-chloro-4-[2-methyl-1-(1-phenyl-ethyl)-1H-imida-
  zol-4-ylethynyl]-pyridine.

The compounds of general formula I and their pharmaceutically acceptable salts can be manufactured by the general procedure, as shown below:

a) reacting a compound of formula

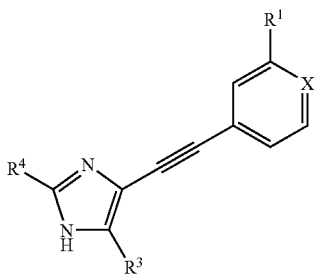

with a compound of formula $R^2$Yhal to form a compound of formula

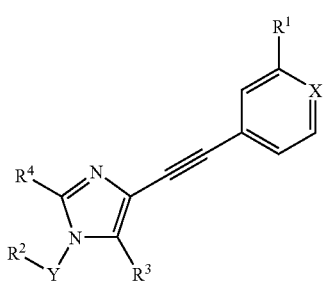

I wherein $R^1$, $R^2$, $R^3$, $R^4$, X and Y are as described above and hal is halogen, preferably chloro, bromo or iodo, and if desired, converting the compounds obtained into pharmaceutically acceptable acid salts.

The starting material are known compounds or may be prepared according to methods known in the art.

The compounds can be synthesized by the procedure shown in the following scheme:

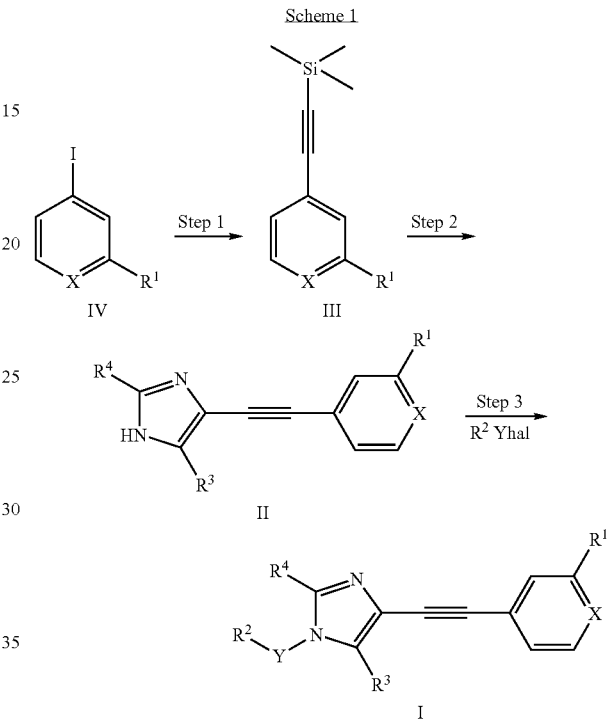

Scheme 1 wherein the definitions of $R^1$, $R^2$, $R^3$, $R^4$, X and Y are as described above.

Step 1

A compound of formula IV, for example 2-chloro-4-iodo-pyridine, is dissolved in dry THF and triethyl amine. This mixture is evacuated and backfdled with argon several times to remove oxygen from the solution. Triphenylphosphine and bis(triphenylphosphine)palladium(II)chloride are added and the reaction mixture is stirred at room temperature for about 1 h. Copper(I)iodide and trimethylsilylacetylene are added. The reaction mixture is stirred at room temperature overnight. The solvent is evaporated and the product of formula III is dried and purified by chromatography.

Step 2

Solution 1: A solution of a compound of formula III, for example 2-chloro-4-trimethylsilanylethynyl-pyridine, and a 2-substituted-5-iodo-1H-imidazole compound (e.g. 5-iodo-2-methyl-1H-imidazole (synthesis: M. D. Cliff, S. G. Pyne, *Synthesis* 1994, 681-682)) are dissolved in dry THF and dry DMF. This mixture is evacuated and backfilled with argon several times to remove oxygen from the solution.

Solution 2: Triphenylphosphine, bis(triphenylphosphine)-palladium(II)chloride, copper(I)iodide and triethyl amine are dissolved in dry THF. This mixture is also evacuated and backfilled with argon several times to remove oxygen from the solution. Solution 2 is heated to 40° C. and solution 1 is added dropwise. The reaction mixture is heated to about 60° C. and tetrabutylammonium fluoride solution is added dropwise during 45 min. The reaction is then stirred at room temperature overnight. The solvent is evaporated, dried and purified by chromatography. A compound of formula II is obtained.

Step 3

Sodium hydride is suspended in THF. A solution of a compound of formula II, for example 2-methyl-4-(2-methyl-1H-imidazol-4-ylethynyl)-pyridine in dry THF is added and the reaction mixture is stirred at room temperature for about 30 min. A corresponding compound of formula $R^2$Yhal, for example 2-(bromomethyl)pyridine hydrobromide, 2-chloromethyl-6-methyl-pyridine hydrochloride or (2-bromoethyl)benzene is added, and stirring is continued overnight. The reaction mixture is poured into water, extracted, dried and purified by flash chromatography and a mixture of two regioisomers of a compound of formula I is obtained. This mixture can be separated by crystallization.

Pharmaceutically acceptable salts of compounds of formula I can be manufactured readily according to methods known in the art and taking into consideration the nature of the compound to be converted into a salt. Inorganic or organic acids such as, for example, hydrochloric acid, hydrobromic acid, sulfuric acid, nitric acid, phosphoric acid or citric acid, formic acid, fumaric acid, maleic acid, acetic acid, succinic acid, tartaric acid, methanesulfonic acid, p-toluenesulfonic acid and the like are suitable for the formation of pharmaceutically acceptable salts of basic compounds of formula I. Compounds which contain the alkali metals or alkaline earth metals, for example sodium, potassium, calcium, magnesium or the like, basic amines or basic amino acids are suitable for the formation of pharmaceutically acceptable salts of acidic compounds.

The compounds of formula I and their pharmaceutically acceptable salts are, as already mentioned above, metabotropic glutamate receptor antagonists and can be used for the treatment or prevention of mGluR5 receptor mediated disorders, such as acute and/or chronic neurological disorders, cognitive disorders and memory deficits, as well as acute and chronic pain. Treatable neurological disorders are for instance epilepsy, schizophrenia, anxiety, acute, traumatic or chronic degenerative processes of the nervous system, such as Alzheimer's disease, senile dementia, Huntington's chorea, ALS, multiple sclerosis, dementia caused by AIDS, eye injuries, retinopathy, idiopathic parkinsonism or parkinsonism caused by medicaments as well as conditions which lead to glutamate-deficient functions, such as e.g. muscle spasms, convulsions, migraine, urinary incontinence, ethanol addiction, nicotine addiction, psychoses, opiate addiction, anxiety, vomiting, dyskinesia and depression. Other treatable indications are restricted brain function caused by bypass operations or transplants, poor blood supply to the brain, spinal cord injuries, head injuries, hypoxia caused by pregnancy, cardiac arrest and hypoglycemia.

The compounds of formula I and their pharmaceutically acceptable salts are especially useful as analgesics. Treatable kinds of pain include inflammatory pain such as arthritis and rheumatoid disease, vasculitis, neuropathic pain such as trigeminal or herpetic neuralgia, diabetic neuropathy pain, causalgia, hyperalgesia, severe chronic pain, post-operative pain and pain associated with various conditions like cancer, angina, renal or billiary colic, menstruation, migraine and gout.

The pharmacological activity of the compounds was tested using the following method:

For binding experiments, cDNA encoding human mGlu 5a receptor was transiently transfected into EBNA cells using a procedure described by Schlaeger and Christensen [Cytotechnology 15:1-13 (1998)]. Cell membrane homogenates were stored at −80° C. until the day of assay where upon they were thawed and resuspended and polytronized in 15 mM Tris-HCl, 120 mM NaCl, 100 mM KCl, 25 mM CaCl$_2$, 25 mM MgCl$_2$ binding buffer at pH 7.4 to a final assay concentration of 20 µg protein/well.

Saturation isotherms were determined by addition of twelve [$^3$H]MPEP concentrations (0.04-100 nM) to these membranes (in a total volume of 200 µl) for 1 h at 4° C. Competition experiments were performed with a fixed concentration of [$^3$H]MPEP (2 nM) and IC$_{50}$ values of test compounds evaluated using 11 concentrations (0.3-10,000 nM). Incubations were performed for 1 h at 40° C.

At the end of the incubation, membranes were filtered onto unifilter (96-well white microplate with bonded GF/C filter preincubated 1 h in 0.1% PEI in wash buffer, Packard BioScience, Meriden, Coon.) with a Filtermate 96 harvester (Packard BioScience) and washed 3 times with cold 50 mM Tris-HCl, pH 7.4 buffer. Nonspecific binding was measured in the presence of 10 µM MPEP. The radioactivity on the filter was counted (3 min) on a Packard Top-count microplate scintillation counter with quenching correction after addition of 45 µl of microscint 40 (Canberra Packard S. A., Züirich, Switzerland) and shaking for 20 min. For functional assays, [Ca$^{2+}$]i measurements were performed as described previously by Porter et al. [Br. J. Pharmacol. 128:13-20 (1999)] on recombinant human mGlu 5a receptors in HEK-293 cells. The cells were dye loaded using Fluo 4-AM (obtainable by FLUKA, 0.2 µM final concentration). [Ca$^{2+}$]i measurements were performed using a fluorometric imaging plate reader (FLIPR, Molecular Devices Corporation, La Jolla, Calif., USA). Antagonist evaluation was performed following a 5 min preincubation with the test compounds followed by the addition of a submaximal addition of agonist.

The inhibition (antagonists) curves were fitted with a four parameter logistic equation giving IC$_{50}$, and Hill coefficient using an iterative non linear curve fitting software (Xcel fit). For binding experiments the Ki values of the compounds tested are given. The Ki value is defined by the following formula:

$$K_i = IC_{50}/[1 + L/K_d]$$

in which the IC$_{50}$ values are those concentrations of the compounds tested which cause 50% inhibition of the competing radioligand ([$^3$H]MPEP). L is the concentration of radioligand used in the binding experiment and the K$_d$ value of the radioligand is empirically determined for each batch of membranes prepared.

The compounds of the present invention are mGluR 5a receptor antagonists.

| Example No. | Ki (nM) |
|---|---|
| 3 | 40 |
| 4 | 93 |
| 18 | 94 |
| 23 | 77 |
| 29 | 33 |

The compounds of formula I and pharmaceutically acceptable salts thereof can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. However, the administration can also be effected rectally, e.g. in the form of suppositories, or parenterally, e.g. in the form of injection solutions.

The compounds of formula I and pharmaceutically acceptable salts thereof can be processed with pharmaceutically inert, inorganic or organic carriers for the production of pharmaceutical preparations. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula I, but as a rule are not necessary. Suitable carriers for suppositories are, for example, natural or hardened oils, waxes, fats, semi-liquid or liquid polyols and the like.

In addition, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

As mentioned earlier, pharmaceutical preparations containing a compound of formula I or pharmaceutically acceptable salts thereof and a therapeutically inert excipient (or a pharmaceutically acceptable carrier) are also an object of the present invention, as is a process for the production of such pharmaceutical preparations which comprises bringing one or more compounds of formula I or pharmaceutically acceptable salts thereof and, if desired, one or more other therapeutically valuable substances into a galenical dosage form together with one or more therapeutically inert carriers.

The dosage can vary within wide limits and will, of course, be fitted to the individual requirements in each particular case. In general, the effective dosage for oral or parenteral administration is between 0.01-20 mg/kg/day, with a dosage of 0.1-10 mg/kg/day being preferred for all of the indications described. The daily dosage for an adult human being weighing 70 kg accordingly lies between 0.7-1400 mg per day, preferably between 7 and 700 mg per day.

The following examples are provided to further elucidate the invention:

EXAMPLE 1

4-[1-(Pyridin-2-ylmethyl)-2-methyl-1H-imidazol-4-ylethynyl]-2-methyl-pyridine

Sodium hydride (69 mg, 55%, 1.59 mmol) was suspended in 2 mL dry THF. A solution of 2-methyl-4-(2-methyl-1H-imidazol-4-ylethynyl)-pyridine (95 mg, 0.48 mmol) in 8 mL dry THF was added and the reaction mixture was stirred at room temperature for 30 min. 2-(Bromomethyl)pyridine hydrobromide (162 mg, 0.63 mmol) was added and stirring was continued overnight. The reaction mixture was poured into 70 mL water and extracted three times with ethyl acetate (70 mL each). The combined organic extracts were dried with sodium sulfate, filtered and evaporated. The crude product was purified by flash chromatography on silica gel (dichloromethane/methanol 100:0→90:10 gradient) and a mixture of two regioisomers was obtained. This mixture could be separated by crystallization from diethylether and the desired compound was obtained as a white solid (35 mg, 25%), MS: m/e=289.1 (M+H$^{30}$).

EXAMPLE 2

4-[1-(Pyridin-2-ylmethyl)-2-methyl-1H-imidazol-4-ylethynyl]-2-chloro-pyridine

The title compound, MS: m/e=309.2 (M+H$^{30}$), was prepared in accordance with the general method of example 1 from 2-chloro-4-(2-methyl-1H-imidazol-4-ylethynyl)-pyridine and 2-(bromomethyl)pyridine hydrobromide.

EXAMPLE 3

2-[4-(3-Chloro-phenylethynyl)-2-methyl-imidazol-1-ylmethyl]-pyridine

The title compound, MS: m/e=308.1 (M+H$^{30}$), was prepared in accordance with the general method of example 1 from 4-(3-chloro-phenylethynyl)-2-methyl-1H-imidazole and 2-(bromomethyl)pyridine hydrobromide.

EXAMPLE 4

4-[1-(6-Methyl-pyridin-2-ylmethyl)-2-methyl-1H-imidazol-4-ylethynyl]-2-methyl-pyridine The title compound, MS: m/e=303.1 (M+H$^{30}$), was prepared in accordance with the general method of example 1 from 2-methyl-4-(2-methyl-1H-imidazol-4-ylethynyl)-pyridine and 2-chloromethyl-6-methyl-pyridine hydrochloride.

EXAMPLE 5

4-[1-(6-Methyl-pyridin-2-ylmethyl)-2-methyl-1H-imidazol-4-ylethynyl]-2-chloro-pyridine The title compound, MS: m/e=323.2 (M+H$^{30}$), was prepared in accordance with the general method of example 1 from 2-chloro-4-(2-methyl-1H-imidazol-4-ylethynyl)-pyridine and 2-chloromethyl-6-methyl-pyridine hydrochloride.

EXAMPLE 6

2-[4-(3-Chloro-phenylethynyl)-2-methyl-imidazol-1-ylmethyl]-6-methyl-pyridine

The title compound, MS: m/e=322.4 (M+H$^{30}$), was prepared in accordance with the general method of example 1 from 4-(3-chloro-phenylethynyl)-2-methyl-1H-imidazole and 2-chloromethyl-6-methyl-pyridine hydrochloride.

EXAMPLE 7

3-[2-Methyl-1-(6-methyl-pyridin-2-ylmethyl)-1H-imidazol-4-ylethynyl]-benzonitrile The title compound, MS: m/e=313.2 (M+H$^{30}$), was prepared in accordance with the general method of example 1 from 3-(2-methyl-1H-imidazol-4-ylethynyl)-benzonitrile and 2-chloromethyl-6-methyl-pyridine hydrochloride.

EXAMPLE 8

4-[1-(2-Methyl-pyridin-5-ylmethyl)-2-methyl-1H-imidazol-4-ylethynyl]-2-chloro-pyridine The title compound, MS: m/e=323.4 (M+H$^{30}$), was prepared in accordance with the general method of example 1 from 2-chloro-4-(2-methyl-1H-imidazol-4-ylethynyl)-pyridine and 5-chloromethyl-2-methyl-pyridine hydrochloride.

EXAMPLE 9

4-[1-(3-Methyl-pyridin-2-ylmethyl)-2-methyl-1H-imidazol-4-ylethynyl]-2-methyl-pyridine The title compound, MS: m/e=303.2 (M+H$^{30}$), was prepared in accordance with the general method of example 1 from 2-methyl-4-(2-methyl-1H-imidazol-4-ylethynyl)-pyridine and 2-chloromethyl-3-methyl-pyridine hydrochloride.

EXAMPLE 10

3-[2-Methyl-1-(3-methyl-pyridin-2-ylmethyl)-1H-imidazol-4-ylethynyl]-benzonitrile The title compound, MS: m/e=313.2 (M+H$^{30}$), was prepared in accordance with the general method of example 1 from 3-(2-methyl-1H-imidazol-4-ylethynyl)-benzonitrile and 2-chloromethyl-3-methyl-pyridine hydrochloride.

EXAMPLE 11

4-[1-(Pyridin-3-ylmethyl)-2-methyl-1H-imidazol-4-ylethynyl]-2-methyl-pyridine

The title compound, MS: m/e=288.9 (M+H$^{30}$), was prepared in accordance with the general method of example 1 from 2-methyl-4-(2-methyl-1H-imidazol-4-ylethynyl)-pyridine and 3-(bromomethyl)pyridine hydrobromide.

EXAMPLE 12

4-[1-(Pyridin-3-ylmethyl)-2-methyl-1H-imidazol-4-ylethynyl]-2-chloro-pyridine

The title compound, MS: m/e=309.3(M+H$^{30}$), was prepared in accordance with the general method of example 1 from 2-chloro-4-(2-methyl-1H-imidazol-4-ylethynyl)-pyridine and 3-(bromomethyl)pyridine hydrobromide.

EXAMPLE 13

3-(2-Methyl-1-pyridin-3-ylmethyl-1H-imidazol-4-ylethynyl)-benzonitrile

The title compound, MS: m/e=299.2 (M+H$^{30}$), was prepared in accordance with the general method of example 1 from 3-(2-methyl-1H-imidazol-4-ylethynyl)-benzonitrile and 3-(bromomethyl)pyridine hydrobromide.

EXAMPLE 14

4-[1-(2-Methyl-pyridin-5-ylmethyl)-2-methyl-1H-imidazol-4-ylethynyl]-2-methyl-pyridine The title compound, MS: m/e=303.2 (M+H$^{30}$), was prepared in accordance with the general method of example 1 from 2-methyl-4-(2-methyl-1H-imidazol-4-ylethynyl)-pyridine and 5-chloromethyl-2-methyl-pyridine hydrochloride.

EXAMPLE 15

5-[4-(3-Chloro-phenylethynyl)-2-methyl-imidazol-1-ylmethyl]-2-methyl-pyridine

The title compound, MS: m/e=322.5 (M+H$^{30}$), was prepared in accordance with the general method of example 1 from 4-(3-chloro-phenylethynyl)-2-methyl-1H-imidazole and 5-chloromethyl-2-methyl-pyridine hydrochloride.

EXAMPLE 16

4-[1-(5-Chloro-pyridin-3-ylmethyl)-2-methyl-1H-imidazol-4-ylethynyl]-2-methyl-pyridine The title compound, MS: m/e=323.1 (M+H$^{30}$), was prepared in accordance with the general method of example 1 from 2-methyl-4-(2-methyl-1H-imidazol-4-ylethynyl)-pyridine and 2-chloro-5-chloromethyl-pyridine.

EXAMPLE 17

4-[1-(2-Chloro-pyridin-5-ylmethyl)-2-methyl-1H-imidazol-4-ylethynyl]-2-methyl-pyridine The title compound, MS: m/e=323.2 (M+H$^{30}$), was prepared in accordance with the general method of example 1 from 2-methyl-4-(2-methyl-1H-imidazol-4-ylethynyl)-pyridine and 3-chloro-5-chloromethyl-pyridine hydrochloride.

EXAMPLE 18

3-[1-(5-Chloro-pyridin-3-ylmethyl)-2-methyl-1H-imidazol-4-ylethynyl]-benzonitrile The title compound, MS: m/e=333.1 (M+H$^{30}$), was prepared in accordance with the general method of example 1 from 3-(2-methyl-1H-imidazol-4-ylethynyl)-benzonitrile and 3-chloro-5-chloromethyl-pyridine hydrochloride.

EXAMPLE 19

4-[1-(Pyridin-4-ylmethyl)-2-methyl-1H-imidazol-4-ylethynyl]-2-methyl-pyridine

The title compound, MS: m/e=333.1 (M+H$^{30}$), was prepared in accordance with the general method of example 1 from 2-methyl-4-(2-methyl-1H-imidazol-4-ylethynyl)-pyridine and 4-(chloromethyl)pyridine hydrochloride.

EXAMPLE 20

4-[1-(2-Methyl-pyridin-4-ylmethyl)-2-methyl-1H-imidazol-4-ylethynyl]-2-chloro-pyridine The title compound, MS: m/e=323.3 (M+H$^{30}$), was prepared in accordance with the general method of example 1 from 2-chloro-4-(2-methyl-1H-imidazol-4-ylethynyl)-pyridine and 4-chloromethyl-2-methyl-pyridine hydrochloride.

EXAMPLE 21

4-(1-Benzyl-2-methyl-1H-imidazol-4-ylethynyl)-2-methyl-pyridine

The title compound, MS: m/e=288.1 (M+H$^{30}$), was prepared in accordance with the general method of example 1 from 2-methyl-4-(2-methyl-1H-imidazol-4-ylethynyl)-pyridine and benzylbromide.

EXAMPLE 22

4-(1-Benzyl-2-methyl-1H-imidazol-4-ylethynyl)-2-chloro-pyridine

The title compound, MS: m/e=308.2 (M+H$^{30}$), was prepared in accordance with the general method of example 1 from 2-chloro-4-(2-methyl-1H-imidazol-4-ylethynyl)-pyridine and benzylbromide.

EXAMPLE 23 rac-2-Methyl-4-[2-methyl-1-(1-phenyl-ethyl)-1H-imidazol-4-ylethynyl]-pyridine The title compound, MS: m/e=302.2 (M+H$^{30}$), was prepared in accordance with the general method of example 1 from 2-methyl-4-(2-methyl-1H-imidazol-4-ylethynyl)-pyridine and (1-bromoethyl)benzene.

EXAMPLE 24

(+)-2-Methyl-4-[2-methyl-1-(1-phenyl-ethyl)-1H-imidazol-4-ylethynyl]-pyridine Rac-2-Methyl-4-[2-methyl-3-(1-phenyl-ethyl)-3H-imidazol-4-ylethynyl]-pyridine was separated into it's enantiomers using chiral HPLC (chiralpac AD, 10% isopropanol in heptane). The enantiomer with the shorter retention time was determined as (+)-enantiomer.

EXAMPLE 25

(−)-2-Methyl-4-[2-methyl-1-(1-phenyl-ethyl)-1H-imidazol-4-ylethynyl]-pyridine rac-2-Methyl-4-[2-methyl-3-(1-phenyl-ethyl)-3H-imidazol-4-ylethynyl]-pyridine was separated into it's enantiomers using chiral HPLC (chiralpac AD, 10% isopropanol in heptane). The enantiomer with the longer retention time was determined as (−)-enantiomer.

EXAMPLE 26 rac-2-Chloro-4-[2-methyl-1-(1-phenyl-ethyl)-1H-imidazol-4-ylethynyl]-pyridine The title compound, MS: m/e=322.1 (M+H$^{30}$), was prepared in accordance with the general method of example 1 from 2-chloro-4-(2-methyl-1H-imidazol-4-ylethynyl)-pyridine and (1-bromoethyl)benzene.

EXAMPLE 27

4-[1-(4-Fluoro-benzyl)-2-methyl-1H-imidazol-4-ylethynyl]-2-methyl-pyridine

The title compound, MS: m/e=306.2 (M+H$^{30}$), was prepared in accordance with the general method of example 1 from 2-methyl-4-(2-methyl-1H-imidazol-4-ylethynyl)-pyridine and 4-fluoro-benzylbromide.

EXAMPLE 28

4-[1-(3,4-Difluoro-benzyl)-2-methyl-1H-imidazol-4-ylethynyl]-2-methyl-pyridine The title compound, MS: m/e=324.2 (M+H$^{30}$), was prepared in accordance with the general method of example 1 from 2-methyl-4-(2-methyl-1H-imidazol-4-ylethynyl)-pyridine and 3,4-difluoro-benzylbromide.

EXAMPLE 29

2-Methyl-4-(2-methyl-1-phenethyl-1H-imidazol-4-ylethynyl)-pyridine

The title compound, MS: m/e=302.2 (M+H$^{30}$), was prepared in accordance with the general method of example 1 from 2-methyl-4-(2-methyl-1H-imidazol-4-ylethynyl)-pyridine and (2-bromoethyl)benzene.

EXAMPLE 30

4-[1-(2-Chloro-pyridin-5-ylmethyl)-2-methyl-1H-imidazol-4-ylethynyl]-2-chloro-pyridine The title compound, MS: m/e=343.1 (M+H$^{30}$), was prepared in accordance with the general method of example 1 from 2-chloro-4-(2-methyl-1H-imidazol-4-ylethynyl)-pyridine and 2-chloro-5-chloromethyl-pyridine.

Synthesis of Intermediates

EXAMPLE A

2-Chloro-4-(2-methyl-1H-imidazol-4-ylethynyl)-pyridine

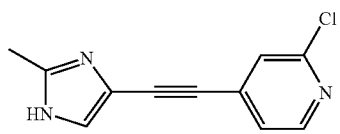

Step 1

2-Chloro-4-trimethylsilanylethynyl-pyridine

2-Chloro-4-iodo-pyridine (10.0 g, 41.8 mmol) was dissolved in 200 mL dry THF and 17.5 mL triethyl amine. This mixture was evacuated and backfilled with argon several times to remove oxygen from the solution. Triphenylphosphine (329 mg, 1.25 mmol) and bis(triphenylphosphine)palladium(II)chloride (1.47 g, 2.09 mmol) were added and the reaction mixture was stirred at room temperature for 1 h.

Copper(I)iodide (239 mg, 1.25 mmol) and trimethylsilylacetylene (6.28 g, 6.39 mmol) were added. The reaction mixture was stirred at room temperature overnight. The solvent was evaporated. The residue was taken up in 500 mL water and extracted three times with ethyl acetate (500 mL each). The combined organic extracts were dried with magnesium sulfate, filtered and evaporated. The crude product was purified by chromatography on silica gel (cyclohexane/ethyl acetate 80:20). The desired product was obtained as a light brown semi solid (10 g, >100%). This material was used without any further purification for the next step.

Step 2

2-Chloro-4-(2-methyl-1H-imidazol-4-ylethynyl)-pyridine

Solution 1: 2-Chloro-4-trimethylsilanylethynyl-pyridine (8.9 g, purity <100% as indicated in step 1) and 5-iodo-2-methyl-1H-imidazole (13.24 g, 64 mmol, synthesis: M. D. Cliff, S. G. Pyne, *Synthesis* 1994, 681-682) were dissolved in 75 mL dry THF and 20 mL dry DMF. This mixture was evacuated and backfilled with argon several times to remove oxygen from the solution.

Solution 2: Triphenylphosphine (223 mg, 0.85 mmol), bis(triphenylphosphine)-palladium(II)chloride (1.79 g, 2.55 mmol), copper(I)iodide (81 mg, 0.43 mmol) and triethyl amine (8.87 mL, 64 mmol) were dissolved in 75 mL dry THF. This mixture was also evacuated and backfilled with argon several times to remove oxygen from the solution Solution 2 was heated to 40° C. and solution 1 was added dropwise. The reaction mixture was heated to 60° C. and tetrabutylammonium fluoride solution (1M in THF, 55 mL, 55 mmol) was added dropwise during 45 min. The reaction was then stirred at room temperature overnight. The solvent was evaporated. The residue was taken up in 200 mL water and extracted three times with ethyl acetate (200 mL each). The combined organic extracts were dried with magnesium sulfate, filtered and evaporated. The crude product was purified by chromatography on silica gel (methylene chloride/methanol 95:5) and recrystallized from a mixture of methylene chloride and ethyl acetate. The desired product was obtained as a light brown solid (2.89 g, 31%).

EXAMPLE B

2-Methyl-4-(2-methyl-1H-imidazol-4-ylethynyl)-pyridine

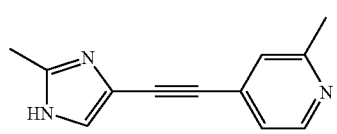

The title compound was prepared in accordance with the general method of example A (step 1 and 2) from 4-iodo-2-methyl-pyridine and 5-iodo-2-methyl-1H-imidazole.

EXAMPLE C 4-(3-Chloro-phenylethynyl)-2-methyl-1H-imidazole

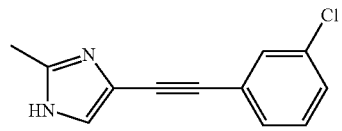

The title compound was prepared in accordance with the general method of example A (step 1 and 2) from 3-chloro-iodobenzene and 5-iodo-2-methyl-1H-imidazole.

EXAMPLE D 3-(2-Methyl-1H-imidazol-4-ylethynyl)-benzonitrile

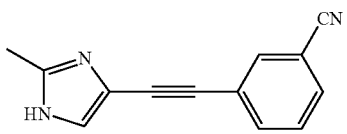

The title compound was prepared in accordance with the general method of example A (step 1 and 2) from 3-bromo-benzonitrile and 5-iodo-2-methyl-1H-imidazole.

EXAMPLE E

2-Chloromethyl-6-methyl-pyridine hydrochloride

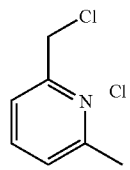

2-(Hydroxymethyl)-6-methylpyridine (3.7 g, 29.4 mmol) was added portion wise at 0° C. to thionylchloride (35 mL, 477 mmol). The reaction mixture was then stirred at room temperature for 18 h. Excess thionylchloride was removed under vacuum and the crude 2-chloromethyl-6-methyl-pyridine hydrochloride (5.1 g, light brown solid) was used without any further purification.

EXAMPLE F

2-Chloromethyl-3-methyl-pyridine hydrochloride

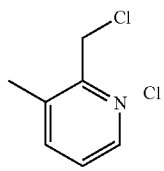

The title compound was prepared in accordance with the general method of example E from 2-(hydroxymethyl)-3-methylpyridine and thionylchloride.

EXAMPLE G

5-Chloromethyl-2-methyl-pyridine hydrochloride

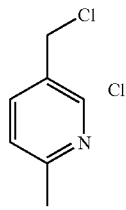

The title compound was prepared in accordance with the general method of example E from 5-(hydroxymethyl)-2-methylpyridine and thionylchloride.

EXAMPLE H

3-Chloro-5-(chloromethyl)pyridine hydrochloride

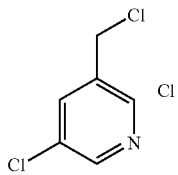

The title compound was prepared in accordance with the general method of example E from 5-(hydroxymethyl)-3-chloropyridine and thionylchloride.

EXAMPLE I

4-Chloromethyl-2-methyl-pyridine hydrochloride

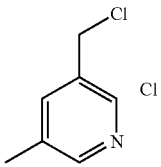

The title compound was prepared in accordance with the general method of example E from 4-(hydroxymethyl)-2-methylpyridine and thionylchloride.

Preparation of the Pharmaceutical Compositions

EXAMPLE I

Tablets of the following composition are produced in a conventional manner:

|  | mg/Tablet |
| --- | --- |
| Active ingredient | 100 |
| Powdered lactose | 95 |
| White corn starch | 35 |
| Polyvinylpyrrolidone | 8 |
| Na carboxymethylstarch | 10 |
| Magnesium stearate | 2 |
| Tablet weight | 250 |

EXAMPLE II

Tablets of the following composition are produced in a conventional manner:

|  | mg/Tablet |
| --- | --- |
| Active ingredient | 200 |
| Powdered lactose | 100 |
| White corn starch | 64 |
| Polyvinylpyrrolidone | 12 |
| Na carboxymethylstarch | 20 |
| Magnesium stearate | 4 |
| Tablet weight | 400 |

EXAMPLE III

Capsules of the following composition are produced:

|  | mg/Capsule |
| --- | --- |
| Active ingredient | 50 |
| Crystalline lactose | 60 |
| Microcrystalline cellulose | 34 |
| Talc | 5 |
| Magnesium stearate | 1 |
| Capsule fill weight | 150 |

The active ingredient having a suitable particle size, the crystalline lactose and the microcrystalline cellulose are homogeneously mixed with one another, sieved and thereafter talc and magnesium stearate are admixed. The final mixture is filled into hard gelatine capsules of suitable size.

What is claimed is:

1. A compound of formula I

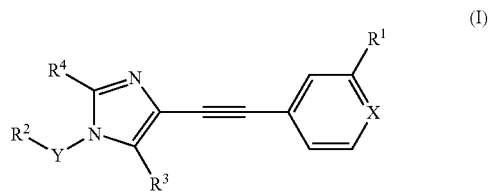

wherein
  $R^1$ is selected from halogen, lower alkyl, lower alkoxy, $CF_3$ and cyano;
  $R^2$ is selected from the group consisting of: pyridyl; pyridyl substituted by lower alkyl; and pyridyl substituted by halogen;
  $R^3$ is selected from hydrogen, C(O)H and $CH_2R^5$, wherein $R^5$ is selected from hydrogen, OH, $C_1$-$C_6$-alkyl and $C_3$-$C_{12}$-cycloalkyl;
  $R^4$ is lower alkyl or $C_3$-$C_{12}$-cycloalkyl;
  X is N;
  Y is —$(CHR)_{1,2\ or\ 3}$; and
  R is hydrogen or lower alkyl;
  or a pharmaceutically acceptable salt thereof.

2. The compound of formula I in accordance with claim 1, wherein the compound is selected from the group consisting of:
  4-[1-(6-methyl-pyridin-2-ylmethyl)-2-methyl-1H-imidazol-4-ylethynyl]-2-methyl-pyridine,
  4-[1-(6-methyl-pyridin-2-ylmethyl)-2-methyl-1H-imidazol-4-ylethynyl]-2-chloro-pyridine, 4-[1-(2-methyl-pyridin-5-ylmethyl)-2-methyl-1H-imidazol-4-ylethynyl]-2-chloro-pyridine,
4-[1-(5-chloro-pyridin-3-ylmethyl)-2-methyl-1H-imidazol-4-ylethynyl]-2-methyl-pyridine,
4-[1-(2-Chloro-pyridin-5-ylmethyl)-2-methyl-1H-imidazol-4-ylethynyl]-2-chloro-pyridine, and
4-[1-(2-chloro-pyridin-5-ylmethyl)-2-methyl-1H-imidazol-4-ylethynyl]-2-methyl-pyridine.

3. A pharmaceutical composition comprising a compound of formula I

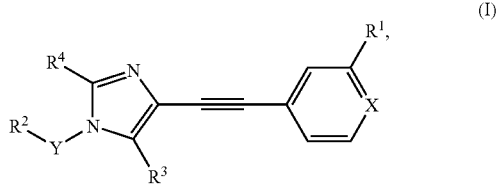

(I)

wherein $R^1$ is selected from halogen, lower alkyl, lower alkoxy, $CF_3$ and cyano;

$R^2$ is selected from the group consisting of: pyridyl; pyridyl substituted by lower alkyl; and pyridyl substituted by halogen;

$R^3$ is selected from hydrogen, C(O)H and $CH_2R^5$, wherein $R^5$ is selected from hydrogen, OH, $C_1$-$C_6$-alkyl and $C_3$-$C_{12}$-cycloalkyl;

$R^4$ is lower alkyl or $C_3$-$C_{12}$-cycloalkyl;

X is N;

Y is —$(CHR)_{1, 2\ or\ 3}$; and

R is hydrogen or lower alkyl; or a pharmaceutically acceptable salt thereof;

and a pharmaceutically acceptable excipient.

* * * * *